US006806386B1

(12) United States Patent
Thommen et al.

(10) Patent No.: US 6,806,386 B1
(45) Date of Patent: Oct. 19, 2004

(54) PROCESS FOR THE PREPARATION OF KETIMINES

(75) Inventors: Marc Thommen, Toffen (SE); Andreas Hafner, Gelterkinden (SE); Frédéric Brunner, Chézard (SE); Hans-Jörg Kirner, Pratteln (DE); Roman Kolly, Allschwill (SE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 16 days.

(21) Appl. No.: 10/130,198

(22) PCT Filed: Nov. 7, 2000

(86) PCT No.: PCT/EP00/10971

§ 371 (c)(1),
(2), (4) Date: May 14, 2002

(87) PCT Pub. No.: WO01/36378

PCT Pub. Date: May 25, 2001

(30) Foreign Application Priority Data

Nov. 16, 1999 (EP) ............................................ 99811054

(51) Int. Cl.⁷ ..................... C07C 209/00; C07C 209/88; C07C 249/02
(52) U.S. Cl. ........................ 564/270; 564/304; 564/308

(58) Field of Search .................................. 564/270, 308, 564/304

(56) References Cited

U.S. PATENT DOCUMENTS

| 4,536,518 A | 8/1985 | Welch, Jr. et al. .......... 514/647 |
| 4,855,500 A | 8/1989 | Spavins ...................... 564/270 |

FOREIGN PATENT DOCUMENTS

| WO | 99/36394 | 7/1999 |
| WO | 99/47486 | 9/1999 |
| WO | 00/26181 | 5/2000 |

OTHER PUBLICATIONS

Houben–Weyl Methoden der Organischen Chemie, vol. E14b, Part I, pp. 239–242.

Primary Examiner—Peter O'Sullivan
(74) Attorney, Agent, or Firm—Kevin T. Mansfield

(57) ABSTRACT

The present invention relates to a process for the preparation of compounds of formula (1), in which $R_1$, $R_2$ and $R_3$ independently of one another are hydrogen, halogen, trifluoromethyl of or $C_1$–$C_4$alkoxy, wherein a compound of formula (2), in which $R_1$, $R_2$ and $R_3$ are as defined in formula (1), is reacted with methylamine in the presence of a non-alcoholic solvent and, if desired, in the presence of a sulfonic acid catalyst to give the compound of formula (2) and, if desired, is subject to purification by recrystallization.

33 Claims, No Drawings

PROCESS FOR THE PREPARATION OF KETIMINES

This application is 371 of PCT/EP00/10971 filed Nov. 17, 2000.

The present invention relates to a process for the preparation of ketimines, which are suitable as starting materials for the preparation of pharmaceutical active compounds having antidepressant properties, for example sertraline.

Processes for the preparation of ketimines are described, for example, in U.S. Pat. No. 4,536,518 or U.S. Pat. No. 4,855,600.

The process for the preparation of ketimines disclosed in U.S. Pat No. 4,536,518 (columns 9/10, Example 1(F)) is characterized in that the ketone is reacted with methylamine with cooling in the presence of titanium tetrachloride in an aprotic solvent, for example tetrahydrofuran. This process has the disadvantage that it has to be carried out using titanium tetrachloride, which is ecologically hazardous. The process procedure is additionally expensive, because the reaction is carried out with cooling. A further disadvantage of this process relates to the work-up. The product must be precipitated using additional hexane.

The process for the preparation of ketimines disclosed in U.S. Pat No. 4,855,500 (columns 5/6, claim 1) comprises reacting the ketone with anhydrous methylamine with cooling in an aprotic solvent, such as, for example, methylene chloride, toluene or tetrahydrofuran in the presence of a molecular sieve.

This process has the disadvantage that the molecular sieve employed is expensive and has to be recycled again in an additional step. A further disadvantage of this process is that the molecular sieve has to be separated off and the product precipitated using additional hexane.

There is therefore furthermore the need to find an efficient process for the preparation of ketimines, which does not have the abovementioned disadvantages.

The present invention therefore relates to a process for the preparation of compounds of the formula

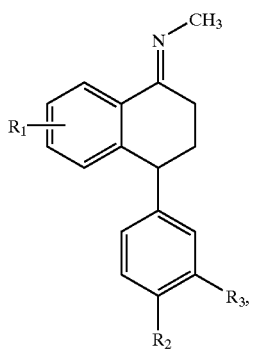
(1)

in which
$R_1$, $R_2$ and $R_3$ independently of one another are hydrogen, halogen, trifluoromethyl or $C_1$–$C_4$alkoxy, wherein a compound of the formula

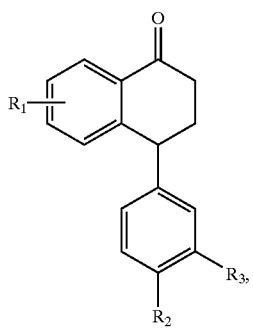
(2)

in which
$R_1$, $R_2$ and $R_3$ are as defined in formula (1) is reacted with methylamine in the presence of a $C_1$–$C_{24}$amine or $C_1$–$C_{12}$nitrile as solvent to give the compound of the formula (1), or is reacted with methylamine in the presence of a sulfonic acid catalyst and of a non-alcoholic solvent to give the compound of the formula (1).

Halogen is, for example, chlorine, bromine or iodine. Chlorine is preferred.

$C_1$–$C_4$alkoxy is a branched or unbranched hydrocarbon radical, for example methoxy, ethoxy, propoxy, isopropoxy, n-butoxy, isobutoxy or tert-butoxy. Methoxy is preferred.

The non-alcoholic solvent preferred for the process according to the invention is preferably selected from (a) $C_1$–$C_{24}$amines,
(b) $C_1$–$C_{12}$nitriles,
(c) $C_2$–$C_{24}$carboxylic acid esters,
(d) $C_3$–$C_{24}$orthoesters,
(e) $C_2$–$C_{24}$ethers,
(f) $C_6$–$C_{24}$alkanes,
(g) aromatic solvents,
(h) amides,
(i) sulfoxides,
(k) halogenated solvents, and
(j) supercritical $CO_2$.

Particularly preferred solvents (a) are selected from aliphatic monoamines, in particular methylamine, nitrogen heterocycles, aliphatic di- and triamines, non-substituted or substituted aromatic monoamines or aromatic diamines.

Further preferred solvents (a) are those of the formula

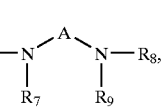
(3)

in which
$R_3$ is hydrogen; $C_1$–$C_5$alkyl; hydroxy-$C_1$–$C_5$alkyl; $C_5$–$C_7$cycloalkyl; phenyl which is not substituted or is substituted by one or more $C_1$–$C_5$alkyl groups, halogen or nitro; phenyl-$C_1$–$C_3$alkyl which is not substituted or is substituted by one or more $C_1$–$C_5$alkyl groups, halogen or nitro;

$R_4$ and $R_5$, independently of one another, are $C_1$–$C_5$alkyl; hydroxy-$C_1$–$C_5$alkyl; $C_5$–$C_7$cycloalkyl; phenyl which is not substituted or is substituted by one or more $C_1$–$C_5$alkyl groups, halogen or nitro; phenyl-$C_1$–$C_3$alkyl which is not substituted or is substituted by one or more $C_1$–$C_5$alkyl groups, halogen or nitro; or $R_4$ and $R_5$ together with the nitrogen atom form a three- to 6-membered heterocyclic radical.

Furthermore, solvents (a) are preferably used which are those of the formula

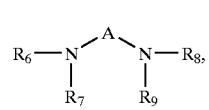
(4)

in which
$R_6$ and $R_8$ independently of one another are hydrogen; $C_1$–$C_5$akyl; or $C_5$–$C_7$cycloalkyl, $R_7$ and $R_9$ independently of one another are $C_1$–$C_5$alkyl; or $C_5$–$C_7$cycloalkyl, phenyl which is not substituted or is substituted by one or more $C_1$–$C_5$alkyl groups, halogen or nitro; phenyl-$C_1$–$C_3$alkyl which is not substituted or is substituted by one or more $C_1$–$C_5$alkyl groups, halogen or nitro; or $R_6$ and $R_7$, $R_8$ and $R_9$ or $R_7$ and $R_9$ form a three- to 6-membered heterocyclic radical; and $A_2$ is $C_1$–$C_5$alkylene.

Exemplary representatives of solvents (a) used according to the invention which may be mentioned are:

as aliphatic monoamines, for example, methylamine, dimethylamine, triethylamine, diethylamine, triethylamine, di-n-propylamine, diisopropylamine, tri-n-propylamine, or triisopropylamine;

as nitrogen heterocycles ethyleneimine, pyrrolidine, piperidine or morpholine, as aliphatic diamines, for example, N,N-dimethylethylenediamine or hexamethylenediamine;

as aromatic monoamines, for example, N-methylaniline or N,N-dimethylaniline;

as substituted aromatic monomamines, for example, o-, m- or p-toluidine, 2-, 3- or 4-chloroaniline, 2-, 3- or 4-nitroaniline;

as aromatic diamines, for example, o-, m- or p-phenylenediamine.

Solvents (b) preferably used are those of the formula

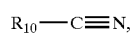

$$R_{10}\!\!-\!\!C\!\equiv\!N, \quad (5)$$

in which $R_{10}$ is straight-chain or branched $C_1$–$C_{12}$alkyl; $C_5$–$C_7$cycloalkyl; phenyl which is not substituted or is substituted by one or more $C_1$–$C_5$akyl groups, halogen or nitro; phenyl-$C_1$–$C_3$alkyl which is not substituted or is substituted by one or more $C_1$–$C_5$alkyl groups, halogen or nitro.

Exemplary representatives of this group are benzonitrile or in particular acetonitrile. Solvents (c) which are preferably used are compounds of the formula

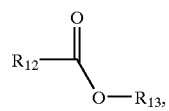

(6)

in which $R_{12}$ and $R_{13}$ independently of one another are straight-chain or branched $C_1$–$C_{12}$alkyl; $C_5$–$C_7$cycloalkyl; or phenyl which is not substituted or is substituted by one or more $C_1$–$C_5$alkyl groups, halogen or nitro; phenyl-$C_1$–$C_3$alkyl which is not substituted or is substituted by one or more $C_1$–$C_5$alkyl groups, halogen or nitro.

Exemplary representatives of these solvents are acetates, such as, for example, methyl acetate or ethyl acetate.

Solvents (d) preferably employed according to the invention are those of the formula

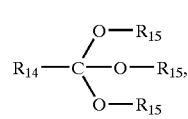

(7)

in which $R_{14}$ is hydrogen; straight-chain or branched $C_1$–$C_5$alkyl; or $C_5$–$C_7$cycloalkyl; and $R_{15}$ is $C_1$–$C_5$alkyl.

Exemplary representatives of these solvents are $C_1$–$C_3$alkyl orthoformates, in particular methyl or ethyl orthoformate or $C_1$–$C_3$alkly orthoacetates, in particular ethyl orthoacetate. Solvents (e) preferably employed according to the invention are those of the formula

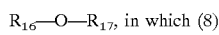

$$R_{16}\!\!-\!\!O\!\!-\!\!R_{17}, \text{ in which} \quad (8)$$

$R_{16}$ and $R_{17}$ independently of one another are hydrogen; straight-chain or branched $C_1$–$C_{12}$alkyl; or $C_5$–$C_7$cycloalkyl; or $R_{16}$ and $R_{17}$ together with the oxygen atom form a 5- to 6-membered radical.

Exemplary representatives of those solvents are dimethyl ether, diethyl ether, methyl ethyl ether, methyl n-propyl ether, methyl i-propyl ether, diisopropyl ether, dibutyl ether or tert-butyl methyl ether. In addition, polyethers can also be employed.

Solvents (f) preferably employed according to the invention are saturated $C_1$–$C_{22}$hydro-carbons, such as, for example, methane, ethane, propane, butane, pentane, hexane, neohexane, heptane, octane, i-octane, nonane, decane, undecane, dodecane, tridecane, tetradecane, pentadecane, hexadecane, heptadecane, octadecane, nonadecane, eicosane, heneicosane or docosane.

Solvents (g) preferably employed according to the invention are in particular benzene, toluene, xylene and xylene isomer mixtures.

Solvents (h) preferably employed according to the invention are in particular aliphatic and aromatic amides of the formula

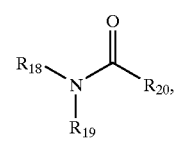

(9)

in which $R_{18}$ and $R_{19}$ independently of one another are hydrogen; $C_1$–$C_5$alkyl; or $C_5$–$C_7$cycloalkyl, and $R_{20}$ is $C_1$–$C_5$alkyl; $C_5$–$C_7$cycloalkyl; phenyl which is not substituted or is substituted by one or more $C_1$–$C_5$alkyl groups, halogen or nitro; or phenyl-$C_1$–$C_3$alkyl which is not substituted or is substituted by one or more $C_1$–$C_5$alkyl groups, halogen or nitro.

Exemplary solvents (i) are those of the formula

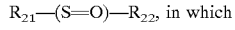

$$R_{21}\!\!-\!\!(S\!\!=\!\!O)\!\!-\!\!R_{22}, \text{ in which} \quad (10)$$

$R_{21}$, and $R_{22}$ independently of one another are $C_1$–$C_5$alkyl; $C_5$–$C_7$cyclalkyl; phenyl which is not substituted or which is substituted by one or more $C_1$–$C_5$alkyl groups, halogen or nitro; or phenyl-$C_1$–$C_3$alkyl which is not substituted or which is substituted by one or more $C_1$–$C_5$alkyl groups, halogen or nitro.

Exemplary solvents (k) are those of the formula $$ClCR_{23}R_{24}R_{25}, \tag{11a}$$

$$Cl_2CR_{26}R_{27} \text{ or} \tag{11b}$$

$$Cl_3\text{—}CR_{28}, \text{in which} \tag{11c}$$

$R_{23}$, $R_{24}$, $R_{25}$, $R_{26}$, $R_{27}$ and $R_{28}$ independently of one another are $C_1$–$C_5$alkyl; $C_5$–$C_7$cycloalkyl; phenyl which is not substituted or which is substituted by one or more $C_1$–$C_5$alkyl groups, halogen or nitro; or phenyl-$C_1$–$C_3$alkyl which is not substituted or which is substituted by one or more $C_1$–$C_5$alkyl groups, halogen or nitro.

Exemplary representatives of this solvent class are dichloroethane, dichloropropane, trichloroethane, furthermore haloaromatics, for example chlorobenzene or dichlorobenzene.

If supercritical $CO_2$ is used, the reaction is carried out at temperatures $T \geq T_{crit}$ and $p \geq p_{crit}$ in $CO_2$ as solvent. After the reaction, $CO_2$ is evaporated and the imine is discharged as solid.

The solvents employed according to the invention can be used as individual compounds or as mixtures of two or more individual compounds of identical or different solvent groups a)–(l).

In addition, there is the possibility of adding further solubilizing or solubility-inhibitng additives (e.g. toluene or cyclohexane)

If the preparation of the compound of the formula (1) is carried out with methylamine in the presence of a $C_1$–$C_{24}$ amine or $C_1$–$C_{12}$nitrile as solvent (with or without catalyst), the conditions and preferences indicated above for the solvent (a) apply for the $C_1$–$C_{24}$amines and those indicated above for the solvent (b) apply for the $C_1$–$C_{12}$nitriles. The use of solvents (b) is preferred here.

Generally, the use of solvents (a) or (b), in particular (b), is preferred.

Suitable sulfonic acid catalysts are, for example, methanesulfonic acid, p-toluenesulfonic acid or camphor-10-sulfonic acid.

A process for the preparation of compounds of the formula (1) is especially preferred in which a sulfonic acid catalyst is used, in particular p-toluenesulfonic acid, methanesulfonic acid or camphor-10-sulfonic acid.

The molar quantitative ratio of the catalyst employed to the methylamine employed is expediently 0.001:1 to 1:1, in particular 0.01:1 to 0.5:1, e.g. 0.05:1 to 0.1:1.

The 1:1 molar quantitative ratio of the catalyst to the methylamine also means that the methylamine can also be employed in the process according to the invention in the form of a salt, for example of methylamine hydrochloride.

The process according to the invention is preferably carried out at a temperature from 20 to 120, in particular 30 to 100° C., if appropriate under slight pressure, and the isolation at a temperature from −20 to 40, in particular 0 to 30° C.

For the preparation of the compound of the formula (1) in the presence of a catalyst, a temperature range from 30 to 80° C., in particular 30 to 70° C. and preferably 30 to 60° C., is preferred.

For the preparation of the compound of the formula (1) without the presence of a catalyst, a temperature range from 50 to 120° C., in particular 70 to 120° C. and preferably 80 to 120° C., is preferred. The upper value of the temperature range preferred here is 110° C., in particular 100° C.

The proportion of sertralone in the reaction mixture is, for example, in the range from 5 to 70, preferably 30 to 60, % by weight.

The reaction is particularly preferably carried out using a large molar excess of methylamine.

A process for the preparation of compounds of the formula (1) is therefore particularly preferred in which the molar quantitative ratio of the compound of the formula (2) to methylamine is 1:1 to 1:1000, in particular 1:1.05 to 1:50, e.g. 1:1.5 to 1:15.

The methylamine can be employed in the form of methylamine gas or as a solution in a non-alcoholic solvent.

A process variant is of very particular interest in which the reaction can be carried out in pure methylamine, in particular under pressure, this compound being employed simultaneously as a solvent and reagent. In this case, customarily no significant amounts of further solvent are employed.

Also of particular interest is a process for the preparation of compounds of the formula (1) in which the compound of the formula (1) is continuously crystallized from the reaction medium during the preparation and then filtered off.

Also of especial interest is a process for the preparation of compounds of the formula (1), in which the filtrate is employed for a further reaction for the preparation of compounds of the formula (1). In this case, the amounts of the compound of the formula (2) and methylamine used are replenished. 2 to 10 recyclings of the filtrate are preferred.

The present process according to the invention is accordingly also suitable as a continuous process for the preparation of the compounds of the formula (1).

The water formed during the process can be bound, if desired, using an additional chemical water-binding agent for example an orthoester, e.g. trimethyl orthoformate.

After reaction is complete, if desired, the compound of the formula (1) obtained can be subjected to purification by recrystallization.

Preferably, for this purification process a solvent is employed which is selected from (a) $C_1$–$C_{24}$amines,
(b) $C_1$–$C_{12}$nitriles,
(c) $C_2$–$C_{24}$carboxylic acid esters,
(d) $C_3$–$C_{24}$orthoesters,
(e) $C_2$–$C_{24}$ethers,
(f) $C_6$–$C_{24}$alkanes,
(g) aromatic solvents,
(h) amides,
(i) sulfoxides,
(k) halogenated solvents,
(l) supercritical $CO_2$,
(m) protic solvents, and
(n) $C_2$–$C_{24}$ketones.

The solvents (a) to (l) are the solvents which are also used for the reaction.

The protic solvent (m) is preferably an alcohol, which in particular is of the formula $$X(OH)_b \tag{12}$$

in which
b is 1, 2, 3 or 4, and
if b is 1,
X is $C_1$–$C_8$alkyl, $C_5$–$C_8$cycloalkyl or —$CH_2CH_2$(OCH$_2$CH$_2$)$_c$R$_{21}$,
0, 1 or 2, and
R$_2$, is $C_1$–$C_4$alkoxy, or
if b is 2,
X is $C_2$–$C_8$alkylene or —CH$_2$CH$_2$(OCH$_2$CH$_2$)$_c$—, where c has the above meaning, or if b is 3,
X is $C_3$–$C_8$alkanetriyl or $N(CH_2CH_2)_3$, or
if b is 4,
X is $C_4$–$C_8$alkanetetrayl.

In the abovementioned definitions of the radicals $R_1$ to $R_{21}$:

$C_1$–$C_{12}$alkyl is a branched or unbranched hydrocarbon radical, for example methyl, ethyl, n-propyl, isopropyl, n-butyl, isobutyl, tert-butyl, 2-ethylbutyl, n-pentyl, isopentyl, 1-methylpentyl, 1,3dimethylbutyl, n-hexyl, 1-methylhexyl, n-heptyl, isoheptyl, 1,1,3,3 tetramethylbutyl, 1-methylheptyl, 3-methylheptyl, n-octyl, 2-ethylhexyl, isooctyl, nonyl, decyl, undecyl or dodecyl.

$C_5$–$C_8$cycloalkyl is, for example, cyclopentyl, cycloheptyl, cyclooctyl or preferably cyclohexyl.

$C_1$–$C_4$alkoxy is a branched or unbranched hydrocarbon radical, for example methoxy, ethoxy, propoxy, isopropoxy, n-butoxy, isobutoxy or tert-butoxy. Methoxy is preferred.

$C_2$–$C_{12}$alkenyl is, for example, allyl, methallyl, isopropenyl, 2-butenyl, 3butenyl, isobutenyl, n-penta-2,4-dienyl, 3-methylbut-2enyl, n-oct-2-enyl, n-dodec-2-enyl, isododecenyl, n-dodec-2-enyl or n-octadec-4-enyl.

$C_3$–$C_{12}$alkynyl is $C_3$–$C_{12}$alkyl or $C_3$–$C_{12}$alkenyl, which is mono- or polydiunsaturated, where the triple bonds can, if desired, be isolated or conjugated with one another or with double bonds, for example 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-pentyn-4-yn-1 -yl, 1,3-hexadiyn-5-yl, 1-octy-8-yl, 1-nonyn-9-yl or 1-decyn-10-yl.

$C_2$–$C_8$alkylene is a branched or unbranched radical, for example ethylene, propylene, trimethylene, tetramethylene, pentamethylene, hexamethylene, heptamethylene or octamethylene.

Alkanetriyl having 3 to 8 carbon atoms is derived, for example, from an alkane having 3 to 8 carbon atoms, in which 3 hydrogen atoms are absent and is, for example $$-CH_2-CH-CH_2-, \quad -CH_2-CH_2-CH-CH_2-,$$
$$-CH_2-CH_2-CH-CH_2-CH_2-, \text{ or}$$
$$-CH_2-CH_2-CH_2-CH-CH_2-CH_2-CH_2-.$$

Glyceryl is preferred.

Alkanetetrayl having 4 to 8 carbon atoms is derived, for example, from an alkane having 4 to 8 carbon atoms, in which 4 hydrogen atoms are absent, and is, for example $$-CH_2-\underset{\underset{CH_2-}{|}}{\overset{\overset{CH_2-}{|}}{C}}-CH_2-, \quad -CH_2-CH-CH-CH_2-,$$
$$-CH_2-CH_2-CH-CH-CH_2- \text{ or}$$
$$-CH_2-CH_2-CH-CH_2-CH-CH_2-CH_2-.$$

Pentaerythrityl is preferred.

A preferred meaning of X (for b=1) is, for example, $C_1$–$C_6$alkyl, in particular $C_1$–$C_4$alkyl, e.g. ethyl or isopropyl.

A preferred meaning of X (for b=2) is, for example, $C_2$–$C_6$alkylene, in particular $C_2$–$C_4$alkylene, e.g. ethylene.

Of particular interest is a process for the preparation of compounds of the formula (1), in which the protic solvent is a compound of the formula (12), in which
b is 1 or 2, and
if b is 1,
X is $C_1$–$C_4$alkyl or $C_5$–$C_6$cycloalkyl, or
if b is2,
X is $C_2$–$C_4$alkylene.

Practically relevant alcohols for the purification step are methanol, ethanol, isopropanol, n-butanol, ethylene glycol, methylcellosolve, cyclohexanol, diethylene glycol or triethanolamine.

Solvents employed for the purification process are furthermore $C_2$–$C_{24}$ketones (=Component (n)), which in particular are those of the formula $$R_{22}\overset{O}{\underset{}{\|}}\!\!-\!\!A_1\!\!-\!\!\left[\overset{O}{\underset{}{\|}}\right]_n\!\!-\!\!R_{23}, \tag{13}$$

in which
$R_{22}$ and $R_{23}$ independently of one another are branched or unbranched $C_1$–$C_{12}$alkyl; $C_5$–$C_7$cycloalkyl; $C_2$–$C_{12}$alkenyl; $C_3$–$C_{12}$alkynyl; phenyl or phenyl-$C_1$–$C_3$alkyl, which is not substituted or is substituted by one or more $C_1$–$C_5$alkyl groups;
$A_1$ is a direct bond; or $C_1$–$C_5$alkylene; and n is 0 or 1.

Exemplary representatives of this group are, for example, aliphatically saturated ketones, such as, for example, propanone (acetone), butanone (methyl ethyl ketone) or 2-pentanone (methyl propyl ketone); cycloaliphatically saturated ketones, for example cyclopentanone, cyclohexanone or cycloheptanone (suberone); aliphatically unsaturated ketones, for example 3buten-2-one, 1,4-pentadien-3-one, 3-pentyn-2-one; aromatic ketones, for example benzophenone; aromatic/aliphatic ketones, for example methyl phenyl ketone (acetophenone) or propiophenone; diketones, for example 2,3-butanedione, 2,4-pentanedione or 2,5-hexanedione; or aromatic diketones, for example diphenylethanedione (benzil).

In a particularly preferred embodiment, the purification is carried out in the same solvent as the reaction.

In a preferred process variant, the purification is carried out by recrystallization of sertraline (compound of the formula (1)) under reflux. For this, the isomerically pure sertraline is introduced in a suitable solvent into a suitable reaction vessel having a stirrer and reflux condenser. The reaction mass is heated to reflux temperature in an inert gas atmosphere with stirring until a clear solution is present. The solution is cooled to the appropriate isolation temperature, the product slowly crystallizing. The suspension is filtered, and the filter cake is washed with the solvent and dried. The imine yield is from 80 to 99%, with a sertralone content of 0.1 to 5.0% (HPLC), a catalyst contamination of $\leq 0.01$ and up to 0.3% water content.

In a further process variant, the recrystallization of sertraline is carried out under pressure. For this, the crude sertraline and the solvent are introduced into a suitable pressure reactor having a stirrer. The reactor is sealed under a nitrogen atmosphere. The stirrer is started and the reaction mixture is heated to the desired reaction temperature until a clear solution is present. The solution is cooled to the appropriate isolation temperature, the product slowly precipitating. The suspension is filtered, and the filter cake is washed with the solvent and dried.

The solution temperatures in the selected solvents are in the range from 30 to 150, preferably 70 to 120° C.

According to the boiling points of the solvents indicated, the purification process can be carried out at normal pressure under reflux or at elevated pressure, normally in the range from 0 to 10, preferably from 0 to 3, bar.

The cooling gradients are in the range from 0.05 to 10, preferably 0.1 to 1, ° C./min.

The isolation temperatures are in the range from −20 to 40, preferably 0 to 25, ° C.

The concentrations of crude sertraline in the clear solution are in the range from 5 to 40, preferably 15 to 20, % by weight.

During the process, adsorbents, for example active carbon or adsorber resins, can be added for the removal of colouring impurities. These adsorbents are added to the clear solution in amounts from 1 to 10% and removed hot by filtration before the crystallization process.

By means of the purification step, both the product purity can be improved and impurities interfering in the further reaction, for example water or catalyst residues, can be separated off.

In a very particularly preferred embodiment, the reaction according to claim 1 is carried out in the presence of a sulfonic acid catalyst and the compound of the formula (1) obtained is subjected to a purification step.

The present invention also relates to a process for the preparation of optically pure (cis) and/or (trans)-sertraline or enantiomerically enriched mixtures of (cis)- and (trans)-sertraline. The process is characterized by the following reaction steps (I)–(III):

(I) reaction of pure sertralone of the formula (2) to give the sertraline of the formula (1) corresponding to the process according to claim 1, (II) subsequent cis-selective hydrogenation with noble metal catalysts or other catalysts based on copper or nickel to give cis-sertraline-enriched mixtures of racemic cis- and trans-sertraline, (III) subsequent mandelic acid-based resolution for the selective preparation of the desired enantiomerically pure cis isomer.

Starting from pure sertralone, sertraline is prepared according to the process described in claim 1. The imine is converted to cis-sertraline-enriched mixtures of racemic cis- and trans-sertraline in a subsequent cis-selective hydrogenation with noble metal catalysts or other catalysts based on copper or nickel on very different supports, such as, for example, carbon, alumina, silica, calcium carbonate, barium carbonate, barium sulfate etc.

In a subsequent mandelic acid-based resolution, the desired enantiomerically pure cis isomers can be crystallized.

The optically pure amine is liberated using sodium hydroxide solution and converted into the desired polymorphic form as the hydrochloride in suitable solvents.

The following examples illustrate the invention further. Details in parts or percentages relate to the weight.

EXAMPLE 1

Preparation of Sertraline in Acetonitrile with Acid Catalysis 240 g of pure sertralone (>99%) and 650 ml of acetonitrile are introduced into a suitable reaction vessel having a stirrer and gas inlet. The stirrer is started, the suspension is cooled to 0° C. and 55 g of methylamine are passed in. After addition of 10 ml of methanesulfonic acid (catalyst), the reaction mass is heated, stirred at 50° C. until the reaction stops and then cooled to 0° C. The suspension is filtered, washed with cold acetonitrile and dried in vacuo.

Yield: 231.4 g (corresponds to 92.5% of theory) of crude sertraline having the following composition:

96.6% sertraline;

2.9% sertralone;

0.5% water.

The product additionally contains traces of methanesulfonic acid derivatives and salts.

EXAMPLE 2

Preparation of Sertraline in Amines with Acid Catalysis at 50° C.

10 g of pure sertralone (>99%) and 23 g of amine are introduced into a suitable reaction vessel having a stirrer and gas inlet The stirrer is started, the suspension is cooled to 0° C. and 3 g of methylamine are passed in. After addition of 0.65 g (0.1 eq) of para-toluene-sulfonic acid (catalyst), the reaction mass is heated to 50° C., stirred until the reaction stops and then cooled to 10° C. The suspension is filtered, washed with cold ethanol and dried in vacuo.

The following yields for various amines as solvents are obtained:

N-Benzyldimethylamine: 9.3 g of sertraline (corresponds to 90% of theory)

Content:

96% imine, 3.8% sertralone, 0.2% water.

The product additionally contains traces of para-toluenesulfonic acid derivatives.

Triethylamine: 8.8 g of sertraline (corresponds to 85% of theory)

Content:

95% imine, 4.8% sertralone, 0.2% water.

The product additionally contains traces of para-toluenesulfonic acid derivatives.

Diethylamine: 8.9 g of sertraline (corresponds to 86% of theory)

Content:

94% imine, 5.9% sertralone, 0.1% water.

The product additionally contains traces of para-toluenesulfonic acid derivatives.

Diisopropylamine: 7.4 g of sertraline (corresponds to 71% of theory)

Content:

93% imine, 6.9% sertralone, 0.1% water.

The product additionally contains traces of para-toluenesulfonic acid derivatives.

Ethyldiisopropylamine: 85 g of sertraline (corresponds to 82% of theory)

Content:

93% imine, 6.9% sertralone, 0.1% water.

The product additionally contains traces of para-toluenesulfonic acid derivatives.

EXAMPLE 3

Preparation of Sertraline without Acid Catalysis at 90° C.

10 g of pure sertralone (>99%) and 23 g of amine are introduced into a suitable reaction vessel having a stirrer and gas inlet. The stirrer is started, the suspension is cooled to 0° C. and 3 g of methylamine are passed In. The reaction mass is heated, stirred at 90° C. until the reaction stops and then cooled to 10° C. The suspension is filtered, washed with cold ethanol and dried in vacuo.

The following results emerge for various amines as solvents:

N-Benzyldimethylamine: 8.5 g of sertraline (corresponds to 81% of theory)

Content:

95% imine, 4.8% sertralone,

02% water

Triethylamine: 9.2 9 of sertraline (corresponds to 88% of theory)

Content:

96% imine, 3.8% sertralone,

02% water.

N-Methylpiperzine: 6.4 g of sertraline (corresponds to 61% of theory)

Content:

97% imine, 2.8% sertralone, 0.2% water.

EXAMPLE 4

Preparation of Sertraline in Methylamine Using a Catalyst at 60° C.

6 g of pure sertralone (>99%) and 0.5 g of para-toluenesulfonic acid are introduced into a suitable pressure reaction vessel (autoclave) having a stirrer and gas inlet. 24 g of methylamine are then injected. The stirrer is started. The reaction mass is heated, kept at 60° C. and then cooled to room temperature. The methylamine is released in a controlled manner and the residual, solid product dried in vacuo.

Yield: 6.9 g of sertraline (corresponds to 99% of theory)

Content:

89% imine,

1% sertralone,

3% water.

7% para-toluenesulfonic acid derivatives.

EXAMPLE 5

Preparation of Sertraline in Methylamine without a Catalyst at 90° C.

6 g of pure sertralone (>99%) are introduced into a suitable pressure reaction vessel (autoclave) having a stirrer and gas inlet. 24 g of methylamine are then injected. The stirrer is started. The reaction mass is heated, kept at 90° C. and then cooled to room temperature. The methylamine is released in a controlled manner and the residual, solid product is dried in vacuo.

Result 6.4 g of sertraline (corresponds to 99% of theory)

Content:

96% imine,

1% sertralone,

3% water.

EXAMPLE 6

Purification of Sertraline in Acetonitrile 200 g of crude sertraline (cf. Example 1) and 3.5 l of acetonitrile are initially introduced into a suitable reaction vessel having a stirrer, nitrogen inlet and reflux condenser. The nitrogen flushing and the stirrer are started and the reaction mixture is heated to reflux temperature until a clear solution is present. The solution is slowly cooled to 20° C., the product precipitating. The suspension is filtered, and the filter cake is washed with the solvent and dried.

Yield: 178 g of sertraline having the following composition (GC analysis):

99.4% sertraline (corresponds to 88.0% of theory), 0.6% sertralone.

Methanesulfonic acid derivatives and salts are no longer detectable.

EXAMPLE 7

Purification of Sertraline in Ethyl Acetate 200 g (0.637 mol) of crude dry sertraline (96.9% purity) are suspended in 1000 ml of ethyl acetate and 8.0 g of active carbon in a suitable reaction container, equipped with a stirrer and reflux condenser. The mixture is stirred under reflux for 1 h. The active carbon is filtered off hot and the clear filtrate is cooled to 0° C. The crystalline suspension is filtered off. The filter cake is dried overnight in vacuo and yields 174 g (89%) of sertraline.

Purity: 99.5%; 0.3% sertralone.

Methanesulfonic acid derivatives and salts are no longer detectable.

EXAMPLE 8

Purification of Sertraline in other Solvents Analogously to the Previous Examples:

Other solvents and mixtures can also be used for the purification of crude sertraline (same conditions as above) and produce a similar product purity and yield (cf. Table 1).

The reaction is carried out by heating under reflux.

TABLE 1

| Solvent used | Yield [%] | Purity [%] | Sertralone content [%] |
| --- | --- | --- | --- |
| 2-Butanone (MEK) | 88 | 99.4 | 0.4 |
| Mixture of ethanol/ toluene (7:3 vol.) | 90 | 99.6 | 0.4 |
| 2-Propanol (IP) | 90 | 99.8 | 0.4 |

Pure ethanol or ethanol denatured with 2% toluene can also be used for the recrystallization of crude sertralone.

The ratio to be employed is: 2 g of crude sertralone in 30 ml of ethanol.

Yield with 86% and 99.4% purity; 0.5% sertralone.

By adjusting the solubility using solubililty-inhibiting compounds such as alkanes and/or low isolation temperatures, N,N-dimethylformamide (DMF), N,N-dimethylacetamide (DMAC) and dimethyl sulfoxide (DMSO) can also be used, which can also be employed pure or in mixtures for the imine formation.

In all solvents used, the catalyst residues are no longer detectable after the recrystallization.

EXAMPLE 9

Recrystallization of Sertraline above the Boiling Point of the Solvent (Under Pressure)

5 g of crude sertraline (product from Example 2) and 15 to 20 ml of ethanol are introduced into a suitable pressure reaction vessel having a stirrer. The reactor is sealed under a nitrogen atmosphere and the stirrer is started. The reaction mixture is heated to about 110° C. until a dear solution is present. The solution is cooled to 25° C., the product slowly precipitating. The suspension is filtered, and the filter cake is washed with cold ethanol and dried.

Yield: 4.55 g (91%) of sertraline having the following composition:

99.4% sertraline 0.6% sertralone.

Water and traces of catalyst are no longer detectable.

If ethyl acetate is used instead of ethanol, a yield of 4.35 g (87%) is obtained.

What is claimed is:

1. A process for the preparation of compounds of the formula

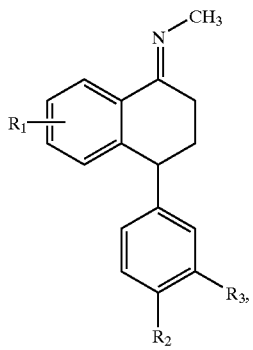

(1)

in which $R_1$, $R_2$ and $R_3$ independently of one another are hydrogen, halogen, trifluoromethyl or $C_1$–$C_4$alkoxy, wherein a compound of the formula

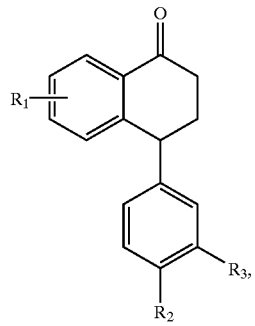

(2)

in which $R_1$, $R_2$ and $R_3$ are as defined in formula (1), is reacted with methylamine in the presence of a sulfonic acid catalyst and of a non-alcoholic solvent to give the compound of the formula (1).

2. A process according to claim 1, wherein a compound of the formula (2) is reacted with methylamine in the presence of a $C_1$–$C_{24}$amine or $C_1$–$C_{12}$nitrile as solvent to give the compound of the formula (1).

3. A process according to claim 1, wherein the non-alcoholic solvent is selected from
  (a) $C_1$–$C_{24}$amines,
  (b) $C_1$–$C_{12}$nitriles,
  (c) $C_2$–$C_{24}$carboxylic acid esters,
  (d) $C_3$–$C_{24}$orthoesters,
  (e) $C_2$–$C_{24}$ethers,
  (f) $C_6$–$C_{24}$alkanes,
  (g) aromatic solvents,
  (h) $C_1$–$C_{24}$amides,
  (i) sulfoxides,
  (k) halogenated solvents, and
  (l) supercritical $CO_2$.

4. A process according to claim 3, wherein the $C_1$–$C_{24}$amines used as solvents are methylamine, nitrogen heterocycles, or aliphatic or aromatic non-substituted or substituted secondary or tertiary mono-, di- or triamines.

5. A process according to claim 4, wherein the $C_1$–$C_{24}$amines used are compounds of the formula

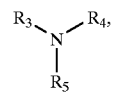

(3)

in which $R_3$ is hydrogen; $C_1$–$C_5$alkyl; hydroxy-$C_1$–$C_5$alkyl; $C_5$–$C_7$cycloalkyl; phenyl which is not substituted or is substituted by one or more $C_1$–$C_5$alkyl groups, halogen or nitro; phenyl-$C_1$–$C_3$alkyl which is not substituted or is substituted by one or more $C_1$–$C_5$alkyl groups, halogen or nitro;

$R_4$ and $R_5$, independently of one another, are $C_1$–$C_5$alkyl; $C_5$–$C_7$cycloalkyl; hydroxy-$C_1$–$C_5$alkyl; phenyl which is not substituted or is substituted by one or more $C_1$–$C_5$alkyl groups, halogen or nitro; phenyl-$C_1$–$C_3$alkyl which is not substituted or is substituted by one or more $C_1$–$C_5$alkyl groups, halogen or nitro; or $R_4$ and $R_5$ together with the nitrogen atom form a 3- to 6-membered heterocyclic radical.

6. A process according to claim 4, wherein the $C_1–C_{24}$amines used are compounds of the formula

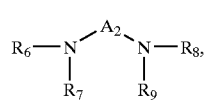
(4)

in which
$R_6$ and $R_8$ independently of one another are hydrogen; $C_1–C_5$alkyl; or $C_5–C_7$cycloalkyl,
$R_7$ and $R_9$ independently of one another are $C_1–C_5$alkyl; or $C_5–C_7$cycloalkyl, phenyl which is not substituted or is substituted by one or more $C_1–C_5$alkyl groups, halogen or nitro; phenyl-$C_1–C_3$alkyl which is not substituted or is substituted by one or more $C_1–C_5$alkyl groups, halogen or nitro; or $R_6$ and $R_7$, $R_8$ and $R_9$ or $R_7$ and $R_9$ form a 3- to 6-membered heterocyclic radical; and $A_2$ is $C_1–C_5$alkylene.

7. A process according to claim 3, wherein the $C_1–C_{12}$nitriles used as solvents are compounds of the formula

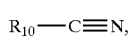
(5)

in which
$R_{10}$ is straight-chain or branched $C_1–C_{12}$alkyl; $C_5–C_7$cycloalkyl; phenyl which is not substituted or is substituted by one or more $C_1–C_5$alkyl groups, halogen or nitro; phenyl-$C_1–C_3$alkyl which is not substituted or is substituted by one or more $C_1–C_5$alkyl groups, halogen or nitro.

8. A process according to claim 3, wherein the solvents (c) used are compounds of the formula

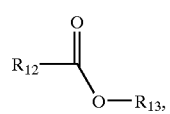
(6)

in which
$R_{12}$ and $R_{13}$ independently of one another are straight-chain or branched $C_1–C_{12}$alkyl; $C_5–C_7$cycloalkyl; or phenyl which is not substituted or is substituted by one or more $C_1–C_5$alkyl groups, halogen or nitro; phenyl-$C_1–C_3$alkyl which is not substituted or is substituted by one or more $C_1–C_5$alkyl groups, halogen or nitro.

9. A process according to claim 3, wherein the solvents (d) used are compounds of the formula

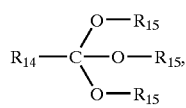
(7)

in which
$R_{14}$ is hydrogen; straight-chain or branched $C_1–C_5$alkyl; or $C_5–C_7$cycloalkyl; and
$R_{15}$ is $C_1–C_5$akyl.

10. A process according to claim 3, wherein the solvents (e) used are compounds of the formula

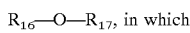
(8)

$R_{16}$ and $R_{17}$ independently of one another are hydrogen; straight-chain or branched $C_1–C_{12}$alkyl; or $C_5–C_7$cycloalkyl; or $R_{16}$ and $R_{17}$ together with the oxygen atom form a 5- to 6 membered radical.

11. A process according to claim 3, wherein the solvents (f) used are saturated $C_1–C_{22}$hydrocarbons.

12. A process according to claim 3, wherein the solvents (g) are selected from benzene, toluene, xylene and xylene isomer mixtures.

13. A process according to claim 1, wherein the compound of the formula (1) is recrystallized from the reaction medium continuously during the preparation and then filtered off.

14. A process according to claim 13, wherein the filtrate is employed for a further reaction for the preparation of the compound of the formula (1).

15. A process according to claim 1, wherein the molar quantitative ratio of the compound of the formula (2) to methylamine is 1:1 to 1:1000.

16. A process according to claim 1, wherein the reaction is carried out at a temperature from 20 to 120° C. and the isolation is carried out at a temperature from –20° C. to 40° C.

17. A process according to any one of claims 1 to 16, wherein the reaction is carried out at elevated pressure.

18. A process according to claim 1, wherein the sulfonic acid catalyst is p-toluenesulfonic acid, methanesulfonic acid or camphor-10-sulfonic acid.

19. A process according to claim 1, wherein the compound of the formula (1) obtained is subjected to purification by recrystallization using a solvent.

20. A process according to claim 19, wherein the solvent is selected from
(a) $C_1–C_{24}$amines,
(b) $C_1–C_{12}$nitriles,
(c) $C_2–C_{24}$carboxylic acid esters,
(d) $C_3–C_{24}$orthoesters,
(e) $C_2–C_{24}$ethers,
(f) $C_6–C_{24}$alkanes,
(g) aromatic solvents,
(h) amides,
(i) sulfoxides,
(k) halogenated solvents,
(l) supercritical $CO_2$,
(m) protic solvents, and
(n) $C_2–C_{24}$ketones.

21. A. A process according to claim 20, wherein the protic solvent (m) is an alcohol.

22. A process according to claim 20, wherein the protic solvent (m) is selected from methanol, ethanol, isopropanol, n-butanol, ethylene glycol, methylcellosolve, cyclohexanol, diethylene glycol, triethanolamine and polyethylene glycol.

23. A process according to claim 20, wherein the solvent (s) are selected from compounds of the formula

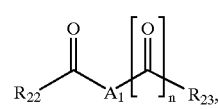
(13)

in which
$R_{22}$ and $R_{23}$ independently of one another are branched or unbranched $C_1–C_{12}$alkyl; $C_5–C_7$cycloalkyl;

$C_2$–$C_{12}$alkenyl; $C_3$–$C_{12}$alkynyl; phenyl or phenyl-$C_1$–$C_3$alkyl, which is not substituted or is substituted by one or more $C_1$–$C_5$alkyl groups;

$A_1$ is a direct bond; or $C_1$–$C_5$alkylene; and n is 0 or 1.

24. A process according to claim 19, wherein the purification is carried out in the same solvent as the reaction itself.

25. A process according to claim 19, wherein the purification is carried out under reflux.

26. A process according to claim 19, wherein the purification is carried out at elevated pressure.

27. A process according to claim 19, wherein the purification is carried out at a temperature of $\leq 150°$ C.

28. A process according to claim 19, wherein the cooling gradient is in the range from 0.05 to 10° C./min.

29. A process according to claim 19, wherein the isolation temperature is in the range from −20 to 40° C.

30. A process according to claim 19, wherein the recrystallization is carried out at elevated pressure.

31. A process according to claim 1, wherein the reaction is carried out in the presence of a sulfonic acid catalyst and the compound of the formula (1) obtained is subjected lo a purification step.

32. A process according to claim 1, wherein the starting compound of the on has a purity of >99%.

33. A process for the preparation of optically pure (cis)- and/or (trans)-sertraline or enantiomerically enriched mixtures of (cis)- and (trans)-sertraline, which comprises the following reaction steps (I)–(III):

(I) reaction of pure sertralone of the formula (2) to give the sertraline of the formula (1) according to the process according to claim 1, (II) subsequent cis-selective hydrogenation with noble metal catalyst or other catalysts based on copper or nickel to give cis-sertraline-enriched mixtures of racemic cis- and trans-sertraline, and (III) subsequent mandelic acid-based resolution for the selective preparation of the desired enantiomerically pure cis isomer.

* * * * *